(12) United States Patent
Avnery et al.

(10) Patent No.: US 6,756,597 B2
(45) Date of Patent: Jun. 29, 2004

(54) FLUID STERILIZATION APPARATUS

(75) Inventors: Tzvi Avnery, Winchester, MA (US); Kenneth P Felis, Stowe, VT (US)

(73) Assignee: Advanced Electron Beams, Inc., Wilmington, MA (US)

( * ) Notice: Subject to any disclaimer, the term of this patent is extended or adjusted under 35 U.S.C. 154(b) by 0 days.

(21) Appl. No.: 10/005,194

(22) Filed: Dec. 4, 2001

(65) Prior Publication Data

US 2002/0088948 A1 Jul. 11, 2002

Related U.S. Application Data

(60) Provisional application No. 60/251,210, filed on Dec. 4, 2000.

(51) Int. Cl.[7] ................................................ G21G 5/00
(52) U.S. Cl. ................... 250/433; 250/492.3; 210/386; 210/402
(58) Field of Search .................. 250/433, 494.1–494.3; 210/386, 402; 361/225–230

(56) References Cited

U.S. PATENT DOCUMENTS

| | | | |
|---|---|---|---|
| 2,340,890 A | 2/1944 | Lang et al. ................... 250/48 |
| 3,655,965 A | 4/1972 | Icre et al. ..................... 250/45 |
| 3,891,855 A | 6/1975 | Offermann ................... 250/492 |
| 3,901,807 A | 8/1975 | Trump ......................... 210/198 |
| 3,974,391 A | 8/1976 | Offermann ............. 250/492 B |
| 3,988,588 A | 10/1976 | Offermann ............. 250/492 B |
| 4,038,028 A | * 7/1977 | La Roche .................... 422/186 |
| 4,048,504 A | 9/1977 | Bosshard ..................... 250/434 |
| 4,074,138 A | 2/1978 | Bosshard ..................... 250/435 |
| 4,093,419 A | 6/1978 | Tauber et al. ............. 21/102 R |
| 4,173,719 A | 11/1979 | Tauber et al. ............... 250/310 |
| 4,201,918 A | 5/1980 | Latzer ......................... 250/433 |
| 4,230,947 A | 10/1980 | Cram ........................... 250/434 |
| 5,072,124 A | 12/1991 | Kondo et al. ............ 250/432 R |
| 5,451,790 A | 9/1995 | Enge ............................ 250/436 |
| 5,530,255 A | 6/1996 | Lyons et al. .............. 250/492.3 |
| 5,744,811 A | 4/1998 | Schonberg et al. ....... 250/492.3 |
| 5,807,491 A | 9/1998 | Materi ......................... 210/748 |
| 6,083,387 A | 7/2000 | LeBlanc et al. ............ 210/199 |

FOREIGN PATENT DOCUMENTS

JP          10-165949          6/1998

OTHER PUBLICATIONS

J.P. Moran, "Cost–Effective Red Water Disposal by Electron Beam Radiolysis," *Sci Research Lab*, pp. 1–128 (1994).

Kurucz, C.N., "The Miami Electron Beam Research Facility: A Large Scale Wastewater Treatment Application," *Radiat. Phys. Chem.* 45(2): 299–308 (1995).

Tokunaga, O., and Arai, H., "Application of Electron Beam Irradiation (4) Treatment of Pollutants by Electron Beam Irradiation," *Radiosotropes*, 43(12):781–790 (1994).

* cited by examiner

*Primary Examiner*—John R. Lee
*Assistant Examiner*—James J. Leybourne
(74) *Attorney, Agent, or Firm*—Hamilton, Brook, Smith & Reynolds, P.C.

(57) ABSTRACT

A fluid sterilization apparatus including a sterilization chamber having a cavity therein, and a nozzle for receiving pressurized fluid and directing a spray of the fluid into the cavity. An electron beam generator having an exit window is mounted to the sterilization chamber for directing a beam of electrons through the exit window and into the cavity of the sterilization chamber to irradiate the spray of fluid. The nozzle is configured to direct the spray of fluid substantially parallel and proximate to the exit window.

26 Claims, 5 Drawing Sheets

FLUID STERILIZATION APPARATUS

RELATED APPLICATION(S)

This application claims the benefit of U.S. Provisional Application No. 60/251,210, filed on Dec. 4, 2000. The entire teachings of the above application are incorporated herein by reference.

BACKGROUND

Some waste treatment plants employ electron beam technology for irradiating sewage for sterilization purposes. In a typical application, the sewage is caused to flow over a waterfall and the falling curtain of sewage is irradiated by an electron beam emitted by an electron beam generator. In order to ensure thorough sterilization, extremely large electron beam generators must be employed to penetrate through the falling curtain, typically in the range of 1 to 10 million eV. Other large systems have been employed for irradiating fluids such as water flowing through a piping system. In such systems, the fluid is irradiated while flowing through the piping system.

SUMMARY

The present invention is directed to a fluid sterilization apparatus which does not require a large electron beam generator. The fluid sterilization apparatus includes a sterilization chamber having a cavity therein. A nozzle is included for receiving pressurized fluid and directing a spray of the fluid into the cavity. An electron beam generator having an exit window is mounted to the sterilization chamber for directing a beam of electrons through the exit window and into the cavity of the sterilization chamber to irradiate the spray of fluid. The nozzle is configured to direct the spray of fluid substantially parallel and proximate to the exit window.

In preferred embodiments, the fluid is pumped by a pump and particles in the fluid are filtered from the fluid by a filter. The nozzle directs a thin, flat film of fluid into the sterilization chamber. In one embodiment, the film of fluid is 0.004 to 0.005 inches thick. The cavity of the sterilization chamber includes an outlet through which the sterilized fluid is removed. In one embodiment, the cavity of the sterilization chamber includes a recycling passage for directing a portion of the spray of fluid back for further irradiation. In this embodiment, a wall between the cavity outlet and the recycling passage directs any fluid from the spray of fluid unable to pass over the wall into the recycling passage.

The present invention is also directed to a fluid sterilization apparatus including a container for containing a supply of fluid. A wheel system having circumferential surfaces is rotatably mounted within the container. The wheel system is configured for extending a portion of the wheel system above the supply of fluid with rotation of the wheel system drawing a film of fluid upwardly out of the supply of fluid on the circumferential surfaces. A doctoring member is positioned for controlling the thickness of the film of fluid on the circumferential surfaces of the wheel system. An electron beam generator is positioned for irradiating the film of fluid with a beam of electrons to sterilize the fluid. A fluid removal member is positioned for removing sterilized fluid from the wheel system.

In preferred embodiments, the wheel system includes a first wheel rotatably mounted within the container for drawing the film of fluid from the supply of fluid. In one embodiment, the wheel system further includes a second wheel rotatably contacting the first wheel for receiving fluid from the first wheel to be irradiated by the electron beam generator.

The present invention fluid sterilization apparatus can have a sterilization region and an electron beam generator that are both compact in size. Consequently, the present invention can be made relatively inexpensively in comparison to the large systems in the prior art. When in a compact size, the present invention apparatus is small enough to be easily installed within both new or existing systems or devices requiring fluid sterilization, and in addition, can also be a portable unit.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
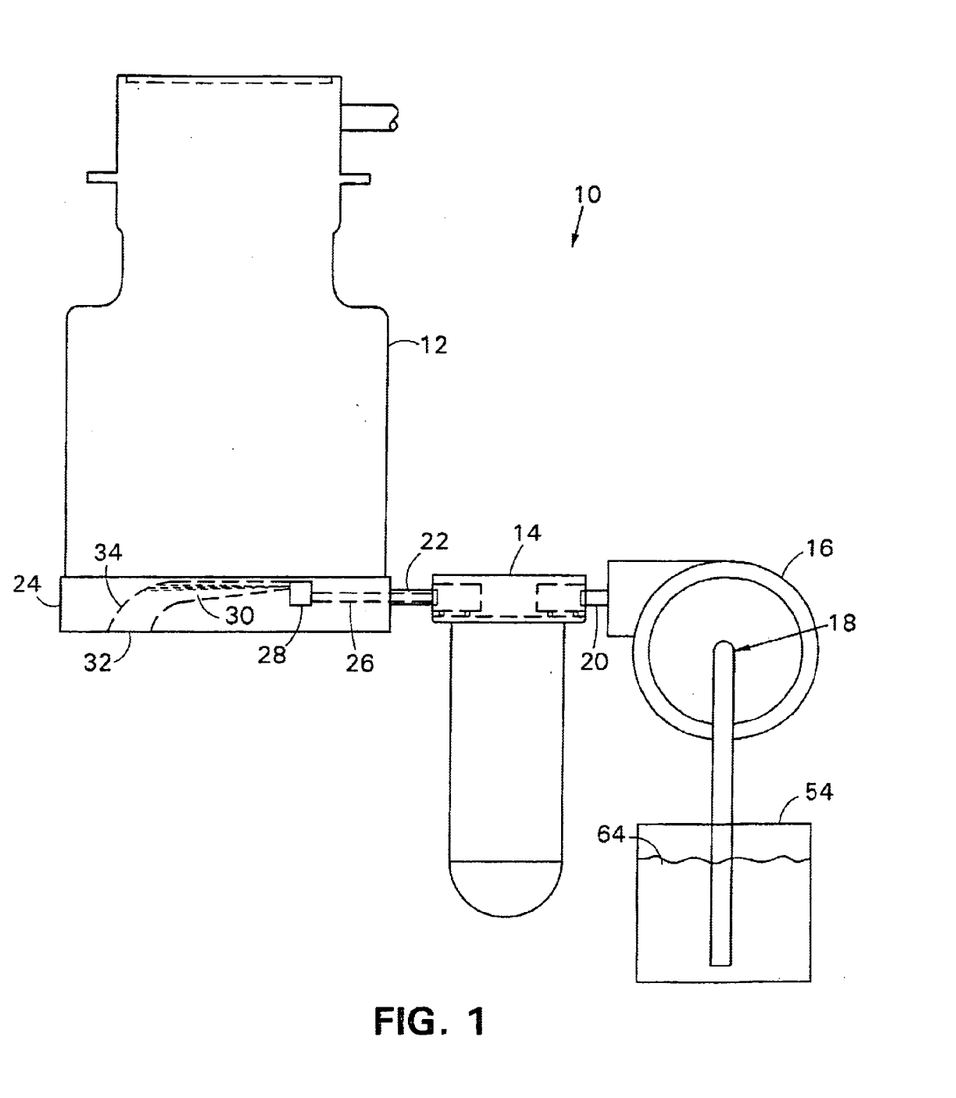
FIG. 1 is a side view of an embodiment of the present invention fluid sterilization apparatus.
Figure 2:
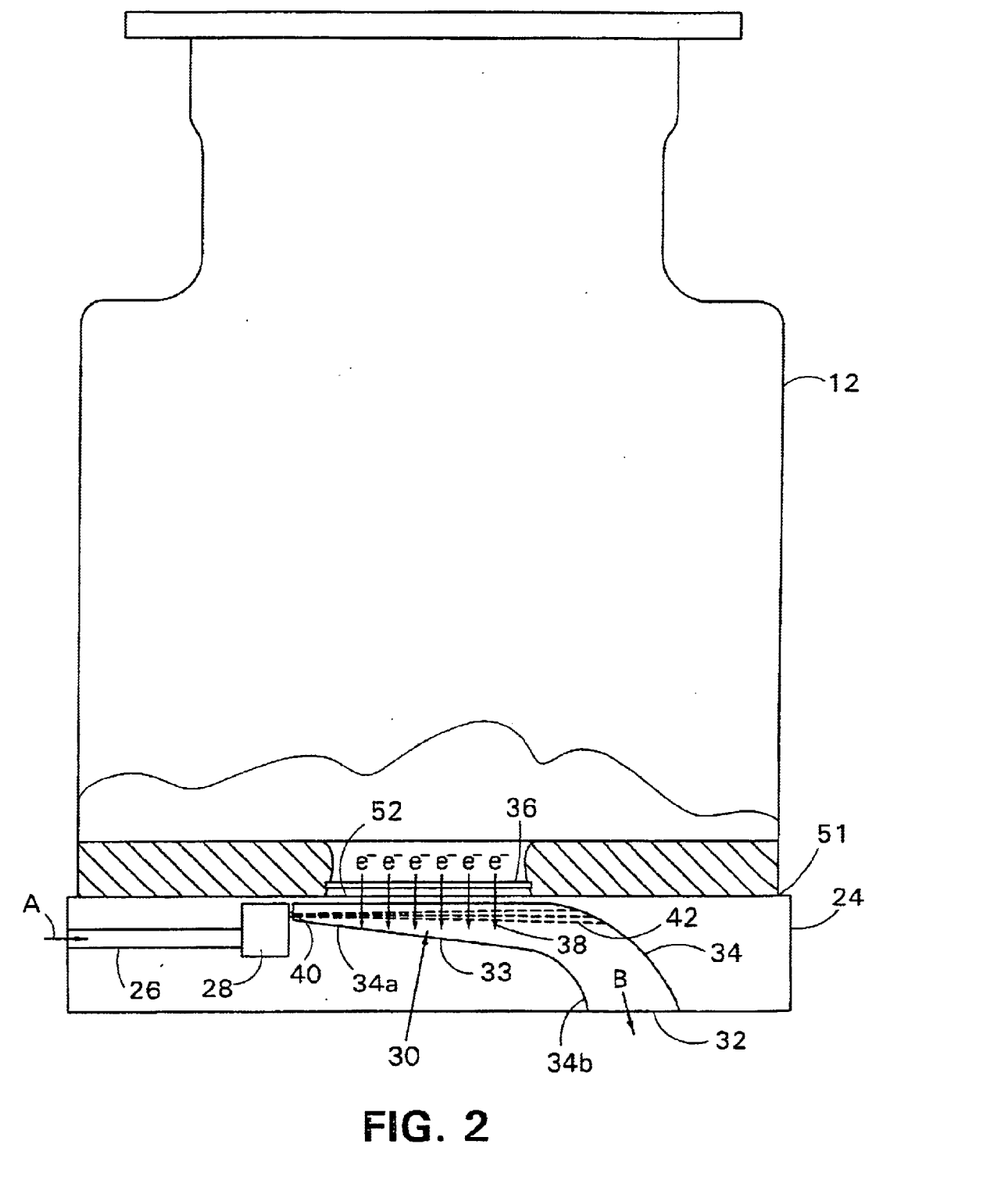
FIG. 2 is an enlarged view of the lower portion of the electron beam generator and the sterilization chamber assembly from the side opposite to that depicted in FIG. 1.
Figure 3:
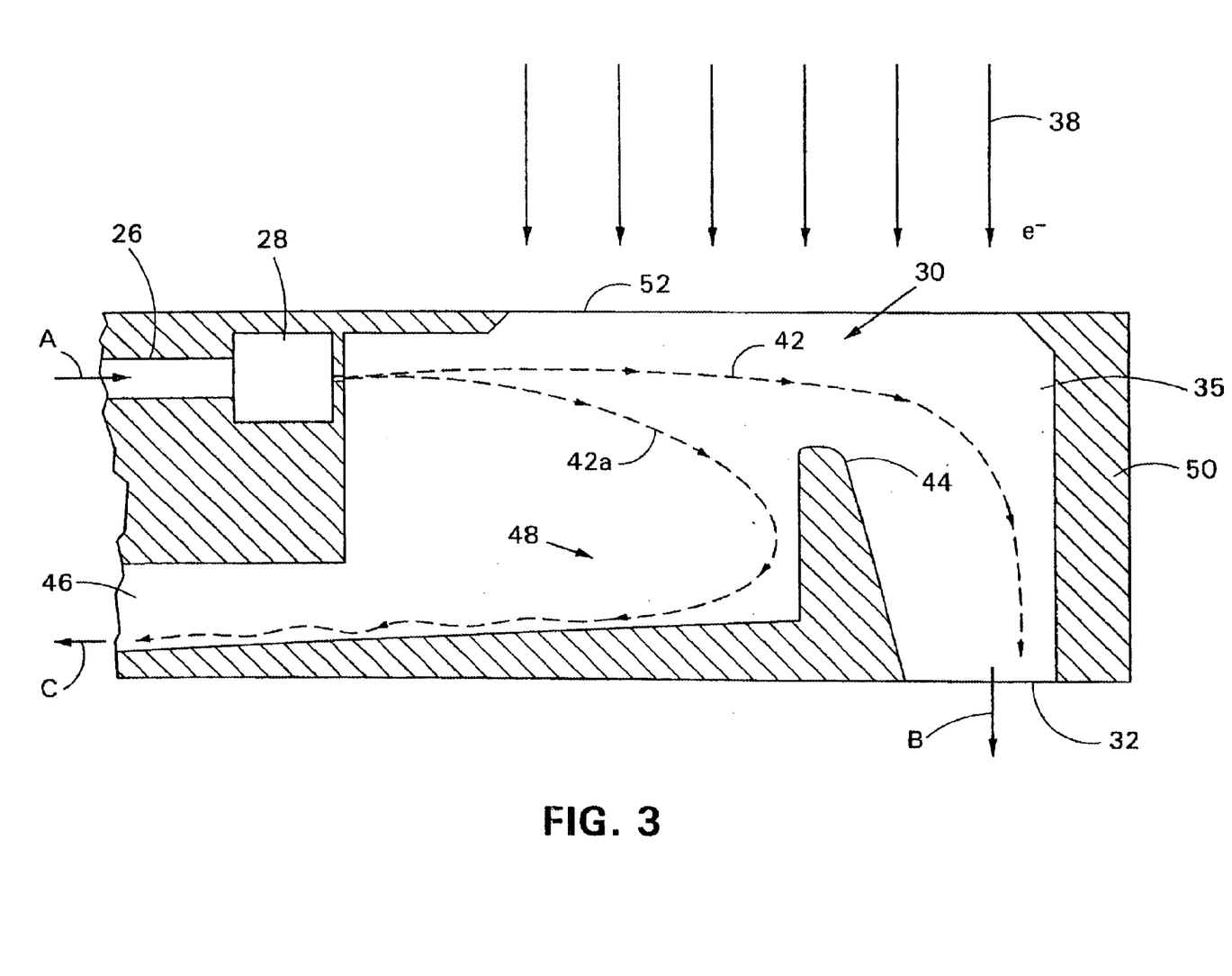
FIG. 3 is a sectional view of a portion of another embodiment of the sterilization chamber.
Figure 4:
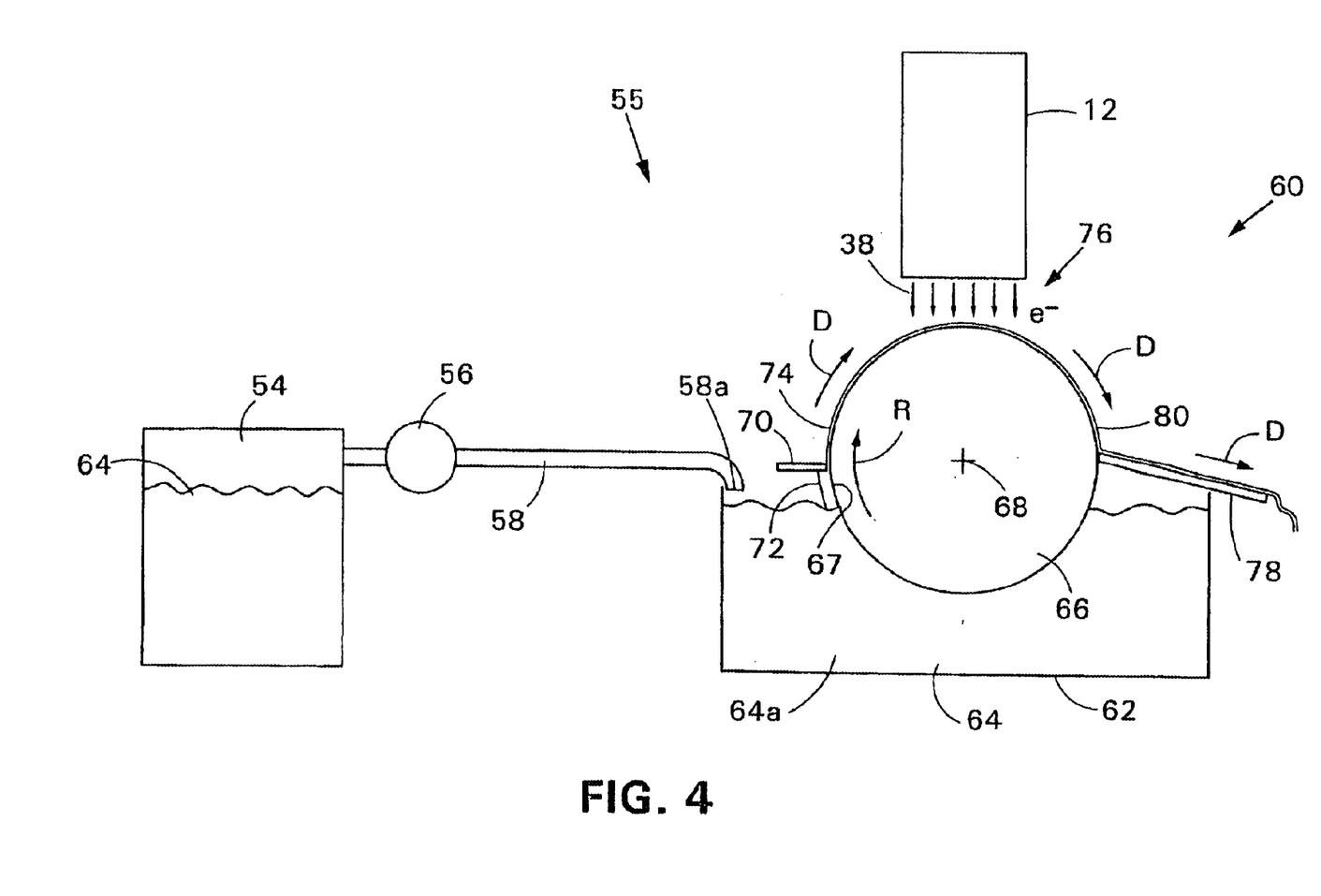
FIG. 4 is a side schematic view of another embodiment of the present invention fluid sterilization apparatus.
Figure 5:
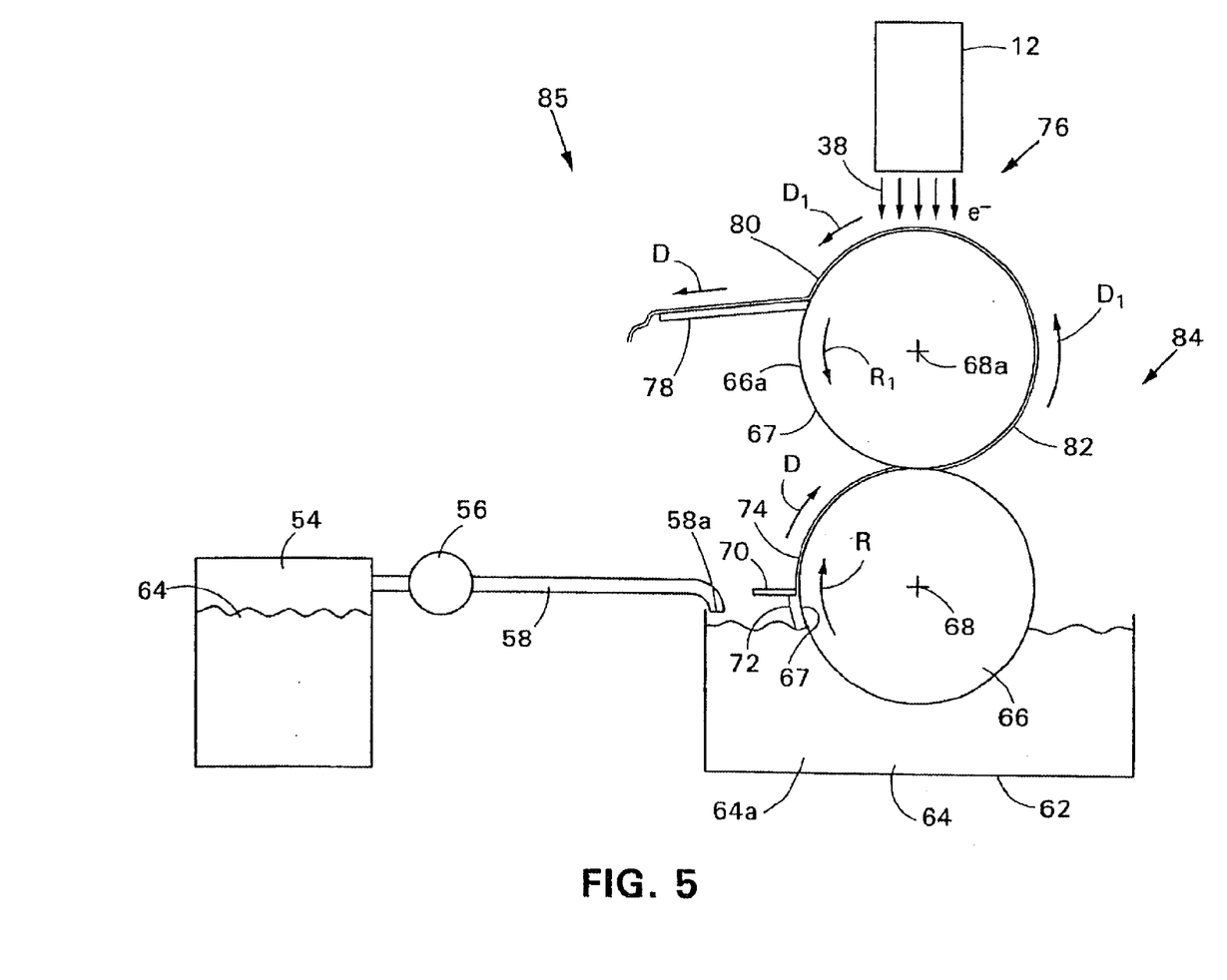
FIG. 5 is a side schematic view of still another embodiment of the present invention fluid sterilization apparatus.

Referring to FIGS. 1 and 2, fluid sterilization apparatus 10 is an embodiment of the present invention that is employed for sterilizing fluid. Such fluids 42 can include water, cooling fluid for machinery, etc. Fluid sterilization apparatus 10 includes a pump 16 for pumping fluid 64 to be sterilized from a fluid reservoir 54 (FIG. 1), a filter 14 for filtering particles from the fluid 64, a reaction or sterilization chamber 24 into which the fluid 64 is sprayed for sterilization, and an electron beam generator 12 that is mounted to sterilization chamber 24 for irradiating the fluid 64 with an electron beam 38 (FIG. 2). The electron beam generator 12 includes an exit window 36 through which an electron beam 38 is directed, and the sterilization chamber 24 includes a nozzle 28 which is aimed into a cavity or passage 34 within sterilization chamber 24. Fluids 64 to be sterilized are introduced as a spray 42 of fluid 64 by nozzle 28 which is directed into cavity 34 proximate to the exit window 36 of the electron beam generator 12 (FIG. 2). The electron beam 38 from the electron beam generator 12 irradiates the spray 42 of fluid 64 with elections e⁻ within cavity 34 thereby sterilizing the fluid 64 by killing organisms, viruses and bacteria in the fluid 64. The sterilized fluid 64 can then be recovered for reuse or disposal from fluid outlet 32.

A more detailed description of fluid sterilization apparatus 10 now follows. Pump 16 has a fluid inlet 18 for pumping the fluid 64 that is to be sterilized from fluid reservoir 54 (FIG. 1). Pump 16 provides pressurized fluid 64 to filter 14 which is coupled to the pump 16 by a fluid conduit 20. The filtered fluid 64 is provided to sterilization chamber 24 through a fluid conduit 22 coupled between filter 14 and sterilization chamber 24.

The filtered fluid 64 enters sterilization chamber 24 under pressure through passage 26, as shown by arrow A (FIG. 2). The passage 26 is in fluid communication with nozzle 28 which is upstream from cavity 34. Typically, the nozzle 28 is configured to produce a spray 42 of fluid 64 into cavity 34 that is a relatively flat, thin, and horizontal film of fluid 64. The spray 42 of fluid 64 enters cavity 34 via entrance 40 and may widen in thickness slightly while passing through cavity 34, as shown. The nozzle 28 in one embodiment consists of a single nozzle such as a horizontal slot for producing a thin flat film of fluid that is about 0.004 to 0.020 inches thick. The nozzle assembly can also be an opening about 0.004 to 0.020 inches in diameter for forming a spray of fluid 42 about 0.004 to 0.020 inches thick. Alternatively, nozzle 28 can have a series of horizontally arranged nozzles.

Cavity 34 has a first portion 34*a* adjacent to nozzle 28 which is generally shallow and formed in the upper portion of sterilization chamber 24 that is closest to the exit window 36 of electron beam generator 12. In FIGS. 1 and 2, the first portion 34*a* is shown to be elongated. The first portion 34*a* of cavity 34 has an upper area forming a reaction or sterilization region 30 through which the spray 42 of fluid is directed and a lower wall 33 which slopes downwardly into fluid outlet 32 located at a second portion or downstream end 34*b* of the cavity 34. The upper portion of cavity 34 is relatively horizontal or parallel to the exit window 36 of election beam generator 12 to allow the spray 42 of fluid 64 to pass through horizontally or parallel to exit window 36. The spray 42 of fluid 64 typically is within 1 inch of exit window 36 with about ¼ inch being more preferable. The slope of lower wall 33 of cavity 34 allows any fluid 64 thereon to flow downwardly toward fluid outlet 32. Typically, sterilization chamber 24 is formed of stainless steel, but alternatively, can be formed of other suitable materials.

A mounting/sealing arrangement 51 between the electron beam generator 12 and the sterilization chamber 24 mounts and seals electron beam generator 12 and the sterilization chamber 24 together in a manner where exit window 36 is sealed above cavity 34 in close proximity thereof (FIG. 2). The exit window 36 of electron beam generator 12 is positioned over sterilization region 30. An irradiation window or opening 52 into cavity 34 faces the exit window 36 of electron beam generator 12 to allow entry of the electron beam 38 into cavity 34. Cavity 34 is enclosed and sealed from the exterior environment so that external contaminants other than fluid 64 cannot enter, whereby cavity 34 can remain relatively sterile during operation. The electron beam generator 12 is typically of a design that is hermetically sealed and may be similar to those described in U.S. Pat. No. 5,962,995, U.S. patent application Ser. No. 09/349,592, filed Jul. 9, 1999, and U.S. patent application Ser. No. 09/209,024, filed Dec. 10, 1998, the contents of which are incorporated herein by reference in their entirety. Usually, electron beam generator 12 operates in the range of 125 kv to 300 kv. Alternatively, other suitable electron beam generators can be employed as well as voltages below 125 kv and above 300 kv.

When the spray 42 of fluid 64 is directed into the cavity 34 of sterilization chamber 24 (FIG. 2), the electrons $e^-$ of the electron beam 38 penetrate the spray 42 of fluid 64 and damage or destroy structures of any organisms, bacteria or viruses within the fluid. This disables or kills the organisms, bacteria or viruses, thereby sterilizing the fluid. In some cases, chemical contaminants in the fluid can also be destroyed. The nozzle 28 is configured and positioned relative to cavity 34 and electron generator 12 to direct the spray 42 of fluid 64 substantially parallel and proximate to the exit window 36 of electron beam generator 12 as well as perpendicular to electron beam 38, for maximum irradiation by electron beam 38. This positions the spray 42 as close as possible to the exit window 36 to be irradiated by the electron beam 38 where the intensity is greatest and the exposure time is the longest. Since cavity 34 is typically occupied by air, the intensity of the electron beam 38 decreases with increasing distance from the exit window 36. In addition, having a thin, flat, film spray 42 of fluid 64 allows maximum penetration through the fluid 64 by the electron beam 38 for thorough sterilization. Making the spray 42 of fluid 64 into a thin flat film 0.004 to 0.020 inches thick allows the electron beams 38 of electron beam generators 12 operating at 125 kv to 300 kv to sufficiently penetrate the spray for sterilization. Typically, the spray 42 of fluid 64 is made about 0.004 inches thick for penetration by an electron beam 38 emitted by an electron beam generator 12 operating at about 125 kv, about 0.005 inches thick at about 150 kv, and about 0.020 inches thick at about 300 kv. A thickness of 0.004 inches to 0.005 inches is the most common for use with electron beam generators 12 operating at 125 kv to 150 kv, respectively. In one embodiment, a low density gas such as helium can be pumped into cavity 34 to increase the range of electron beam 38. Alternatively, cavity 34 can be subjected to a vacuum to increase range.

The sterilized fluid is directed downwardly by the curved rear wall of cavity 34 and then flows downwardly from sterilization chamber 24 through the fluid outlet 32 for recovery or otherwise, as shown by arrow B. This can be back to the fluid reservoir 54 or other desired locations. Pump 16 may be employed to either continuously recirculate fluid for continuous sterilization or may be operated periodically for intermittent sterilization. If only periodic operation is required, fluid sterilization apparatus 10 can be a portable unit which is coupled to the fluid supply for sterilizing the fluid only when needed. In some applications, only weekly sterilization may be required.

In one embodiment, the electron beam generator 12 is about 11 inches in diameter. The combined height of electron beam generator 12 and sterilization chamber 24 for an electron beam generator of such size is about 18.5 inches. Such a small size of a fluid sterilization apparatus 10 allows easy installation within both new and existing systems or devices for sterilizing fluids. The small size also allows fluid sterilization apparatus 10 to be portable. Additionally, fluid sterilization apparatus 10 can be sized to sterilize fluid associated with more than one system or device. In such a case, there may be a central reservoir for the fluid. The fluid inlet 18 and outlet 32 of fluid sterilization apparatus would be arranged in fluid communication with the central reservoir. Also, the size of electron beam generator 12 and sterilization chamber 24 may be increased or decreased for greater or lesser capacity, for example, thicker or thinner sprays 42 of fluid 64. It is apparent that any supply of suitable fluid can be sterilized with fluid sterilization apparatus 10. Typical applications may include but are not limited to sterilizing drinking water or other fluids.

Referring to FIG. 3, sterilization chamber 50 is another preferred sterilization chamber assembly which differs from sterilization chamber 24 in that sterilization chamber 50 includes a cavity 35 having a wall 44 between fluid outlet 32 and a downwardly angled recycling passage 46. Wall 44 forms a collection region 48 which collects or traps any spray 42a of fluid 64 that does not pass over wall 44, usually when nozzle 28 first begins to spray the fluid 64. The fluid 64 collected in collection region 48 typically does not become sufficiently irradiated to an acceptable level of sterilization. Insufficient irradiation can include irradiation by only a portion of electron beam 38 or by passing through electron beam 38 too far away from exit window 36 where the intensity of the electron beam 38 at that distance is decreased. The collected fluid 64 travels down recycling passage 46 in the direction of arrow C for further irradiation. Recycling passage 46 can either bring the fluid 64 back to the fluid reservoir 54 or to a pump which pumps the fluid 64 back into the system just prior to passage 26. The spray 42 of fluid 64 that passes over wall 44 is parallel and proximate to exit window 36, and therefore, becomes sufficiently sterilized by electron beam 38. The sterilized fluid then exits sterilization chamber assembly 50 via fluid outlet 32. The sterilization chamber 50 can be configured so that the sterilization region 30 that is irradiated by electron beam 38 extends downstream or beyond wall 44. The sterilization chamber 50 is designed to be sterilized by operating electron beam generator 12 instead of washing with chemicals. Although wall 44 is shown to have a surface angled toward nozzle 28, alternatively, wall 44 can be straight, curved or have a surface extending away from nozzle 28.

Referring to FIG. 4, fluid sterilization apparatus 55 is another embodiment of the present invention. Fluid sterilization apparatus 55 includes an irradiation assembly 60 that is provided with fluid 64 to be treated from a fluid reservoir 54. The fluid 64 is pumped by pump 56 through conduit 58 and nozzle 58*a* into container 62 of irradiation assembly 60. The container 62 is able to contain a supply 64*a* of the fluid 64. The irradiation assembly 60 includes a wheel system having a wheel 66 that is rotatably mounted within the container 62 about a pivot point 68 for rotation in the direction of arrow R. Wheel 66 can be driven by any suitable conventional means. A portion of the wheel 66 extends above the supply 64*a* of fluid 64. Rotation of the wheel 66 draws an initial film of fluid 72 upwardly out of the supply 64*a* of fluid 64 on the circumferential surfaces 66*a* of wheel 66. A doctoring member or blade 70, typically having a straight edge, is positioned relative to the circumferential surfaces 67 of wheel 66 to control or reduce the thickness of the film 72 to form a thinner film of fluid 74 suitable for irradiation. The doctoring member 70 pushes the excess fluid 64 back down toward the supply 64*a* of fluid 64. Typically, a film of about 0.004 to 0.020 inches in thickness is preferred. The film of fluid 74 travels on wheel 66 in the direction of arrow D and is irradiated with electrons $e^-$ of an electron beam 38 from electron beam generator 12 in a sterilization region 76 to sterilize the film of fluid 74. The film of fluid 74 is sufficiently thin for the electron beam 38 to penetrate in order to kill or destroy organisms, viruses and bacteria. Electron beam generator 12 is similar to that employed in fluid sterilization apparatus 10 and typically operates in the range of 125 kv to 300 kv. After irradiation, the sterilized film of fluid 80 is scraped from wheel 66 by a fluid removal member 78 which contacts the circumferential surfaces 67 of wheel 66 and is angled downwardly to allow the sterilized fluid 80 to be recovered by flowing to a desired location or back to reservoir 54. Typically, the fluid removal member 78 includes a straight edge for contacting wheel 66 and scraping the sterilized fluid 80 therefrom. Sterilization apparatus 55 is designed to cause the fluid 64 to move past electron beam generator 12 and flow only when wheel 66 is rotating since wheel 66 must draw the fluid 64 upwardly out of supply 64*a*. If wheel 66 does not rotate, the fluid stays in container 62. Consequently, when sterilization apparatus 55 is not being operated, the fluid 64 will not leak of flow from container 62. Typically the film of fluid 74 is about 0.004 inches thick for penetration and sterilization by an electron beam 38 emitted by an electron beam generator 12 operating at about 125 kv, about 0.005 inches thick at about 150 kv, and about 0.020 inches thick at about 300 kv. A thickness of 0.004 inches to 0.005 inches is the most common. Alternatively, films of fluid thinner than 0.004 inches and thicker than 0.020 inches can be formed with electron beam generator 12 being appropriately sized for sufficient sterilization. The wheel 66 can be made to have a diameter in the range of about 6 inches to 12 inches so that fluid sterilization apparatus 55 is small enough to be portable. Alternatively, wheel 66 can have smaller or larger diameters.

Referring to FIG. 5, fluid sterilization apparatus 85 is another embodiment of the present invention which differs from fluid sterilization apparatus 55 in that irradiation assembly 84 includes a wheel system having a second wheel 66*a* rotating about pivot point 68*a* and rotatably contacting the first wheel 66 above the supply 64*a* of fluid 64. Typically, wheel 66*a* is driven by wheel 66, but alternatively, can be independently driven. Wheel 66*a* rotates in the direction of arrow $R_1$ and transfers the film of fluid 74 from wheel 66 to wheel 66*a*, becoming a film of fluid 82. The film of fluid 82 moves in the direction of arrow $D_1$, and is irradiated by electron beam 38 from electron beam generator 12. The sterilized film of fluid 80 is then removed from wheel 66*a* by fluid removal member 78. If wheel 66*a* is independently driven, wheel 66*a* can be spaced slightly away from wheel 66 and rotated in either direction.

While this invention has been particularly shown and described with references to preferred embodiments thereof, it will be understood by those skilled in the art that various changes in form and details may be made therein without departing from the scope of the invention encompassed by the appended claims.

For example, although the spray 42 of fluid 64 of fluid sterilization apparatus 10 is shown to be horizontal, alternatively, the spray 42 of fluid 64 and the electron beam generator 12 may be positioned at an angle different from that shown in the figures (such as 90° or 180° and angles in between). Consequently, the terms employed above to describe the present invention such as upper, bottom, horizontal, etc. are used to describe the relative position of components shown and are not meant to limit the orientation of the present invention. In addition, the spray of fluid 42 can have a different configuration such as circular rather than flat. Furthermore, the filter 14 may be positioned upstream of the pump 16. The fluid supplied to the nozzle assembly 28 can be pressurized by means other than pump 16, such as by pressurized gas, by delivering the fluid from the bottom of a reservoir, etc. Also, the fluid sterilization apparatuses described above may be employed for treating fluids for non-sterilization purposes such as curing or initiating chemical reactions, and may treat non-water based fluids. Finally, various components of the different embodiments of the present invention can be combined together or omitted and be sized to suit the application at hand.

What is claimed is:

1. A fluid sterilization apparatus comprising:

a container for containing a supply of fluid;

a wheel system having circumferential surfaces, the wheel system being rotatably mounted within the container, a portion of the wheel system for extending above the supply of fluid with rotation of the wheel system drawing a film of fluid upwardly out of the supply of fluid on the circumferential surfaces;

a doctoring member for controlling the thickness of the film of fluid on the circumferential surfaces of the wheel system;

an electron beam generator for irradiating the film of fluid with a beam of electrons to sterilize the fluid; and a fluid removal member for removing sterilized fluid from the wheel system.

2. The apparatus of claim 1 in which the wheel system comprises a first wheel rotatably mounted within the container for drawing the film of fluid from the supply of fluid.

3. The apparatus of claim 2 in which the wheel system further comprises a second wheel rotatably contacting the first wheel for receiving fluid from the first wheel to be irradiated by the electron beam generator.

4. A method of forming a fluid sterilization apparatus comprising providing a container capable of containing a supply of fluid;

rotatably mounting a wheel system having circumferential surfaces within the container, a portion of the wheel system for extending above the supply of fluid with rotation of the wheel system drawing a film of fluid upwardly out of the supply of fluid on the circumferential surfaces;

providing a doctoring member for controlling the thickness of the film of fluid on the circumferential surfaces of the wheel system;

providing an electron beam generator for irradiating the film of fluid with a beam of electrons to sterilize the fluid; and providing a fluid removal member for removing sterilized fluid from the wheel system.

5. The method of claim 4 further comprising providing the wheel system with a first wheel rotatably mounted within the container for drawing the film of fluid front the supply of fluid.

6. The method of claim 5 further comprising providing the wheel system with a second wheel rotatably contacting the first wheel for receiving fluid from the first wheel to be irradiated by the electron beam generator.

7. A method of sterilizing fluid comprising:

drawing a film of fluid upwardly out of a supply of fluid contained within a container on circumferential surfaces of a rotating wheel system rotatably mounted within the container, a portion of the wheel system extending above the supply of fluid;

controlling the thickness of the film of fluid on the circumferential surfaces of the wheel system with a doctoring member;

irradiating the film of fluid with a beam of electrons from an electron beam generator to sterilize the fluid; and removing the sterilized fluid front the wheel system with a fluid removal member.

8. The method of claim 7 further comprising drawing the film of fluid from the supply of fluid with a first wheel of the wheel system.

9. The method of claim 8 further comprising rotatably contacting a second wheel of the wheel system with the first wheel for receiving thud from the first wheel for irradiation by the electron beam generator.

10. A fluid sterilization apparatus comprising:

a sterilization chamber having a cavity therein;

a nozzle for receiving pressurized fluid and directing a spray of the fluid into the cavity;

an electron beam generator having an exit window, the electron beam generator being mounted to the sterilization chamber for directing a beam of electrons through the exit window into the cavity to the sterilization chamber to irradiate the spray of fluid, the nozzle being configured to direct the spray of fluid substantially parallel and proximate to the exit window; and a pump for pumping the fluid.

11. The apparatus of claim 10 further comprising a filter for filtering particles from the fluid.

12. A fluid sterilization apparatus comprising:

a sterilization chamber having a cavity therein;

a nozzle for receiving pressurized fluid and directing a spray of the fluid into the cavity, the nozzle directing a thin, flat film of fluid about 0.004 to 0.005 inches thick within the sterilization chamber, and an electron beam generator having an exit window, the electron beam generator being mounted to the sterilization chamber for directing abeam of electrons through the exit window into the cavity to the sterilization chamber to irradiate the spray of fluid, the nozzle being configured to direct the spray of fluid substantially parallel and proximate to the exit window.

13. A fluid sterilization apparatus comprising:

a sterilization chamber having a cavity therein, a nozzle for receiving pressurized fluid and directing a spray of the fluid into the cavity, the nozzle directing a thin, flat film of fluid within the sterilization chamber;

an electron beam generator having an exit window, the electron beam generator being mounted to the sterilization chamber for directing a beam of electrons through the exit window into the cavity to the sterilization chamber to irradiate the spray of fluid, the nozzle being configured to direct the spray of fluid substantially parallel and proximate to the exit window; and the cavity of the sterilization chamber including an outlet through which fluid that is sterilized is removed and a recycling passage for directing a portion of the spray of fluid back for further irradiation.

14. The apparatus of claim 13 in which the cavity includes a wall between the cavity outlet and the recycling passage for directing any fluid from the spray of fluid unable to pass over the wall into the recycling passage.

15. A fluid sterilization apparatus comprising:

a sterilization chamber having a cavity therein;

a nozzle for receiving pressurized fluid and for directing a spray of the fluid into the cavity the spray of the fluid being a thin, flat, film of fluid about 0.004 to 0.005 inches thick; and an electron beam generator mounted to the sterilization chamber for directing a beam of electrons into the cavity of the sterilization chamber to irradiate the spray of fluid.

16. A method of forming a fluid sterilization apparatus comprising:

providing a sterilization chamber having a cavity therein;

forming a nozzle for receiving pressurized fluid and directing a spray of the fluid into the cavity;

mounting an electron beam generator to the sterilization chamber, the electron beam generator having an exit window and for directing a beam of electrons through the exit window into the cavity of the sterilization chamber to irradiate the spray of fluid, the nozzle being configured to direct the spray of fluid substantially parallel and proximate to the exit window; and providing a pump for pumping the fluid.

17. The method of claim 16 further comprising providing a filter for filtering particles from the fluid.

18. A method of forming a fluid sterilization apparatus comprising:

providing a sterilization chamber having a cavity therein;

forming a nozzle for receiving pressurized fluid and directing a spray of the fluid into the cavity, the nozzle capable of producing a thin, flu film of fluid about 0.004 to 0.005 inches thick; and mourning an electron beam generator to the sterilization chamber, the electron beam generator having an exit window and for directing a beam of electrons through the exit window into the cavity of the sterilization chamber to irradiate the spray of fluid, the nozzle being configured to direct the spray of fluid substantially parallel and proximate to the exit window.

19. A method of forming a fluid sterilization apparatus comprising:

providing a sterilization chamber having a cavity therein;

forming a nozzle for receiving pressurized fluid and directing a spray of the fluid into the cavity, the nozzle capable of forming a thin, flat film of fluid;

mounting an electron beam generator to the sterilization chamber, the electron beam generator having an exit window and for directing a beam of electrons through the exit window into the cavity of the sterilization chamber to irradiate the spray of fluid, the nozzle being configured to direct the spray of fluid substantially parallel and proximate to the exit window;

fanning the cavity of the sterilization chamber with an outlet through which fluid that is sterilized is removed; and forming a recycling passage in the cavity of the sterilization chamber for directing a portion of the spray of fluid back for further irradiation.

20. The method of claim 19 further comprising forming a wall within the cavity between the cavity outlet and the recycling passage for directing say fluid from the spray of fluid unable to pass over the wall into the recycling passage.

21. A method of sterilizing fluid comprising:

directing a spray of pressurized fluid from a nozzle assembly into a cavity of a sterilization chamber;

irradiating the spray of fluid with a beam of electrons from an electron beam generator mounted to the sterilization chamber, the electron beam generator having an exit window through which the beam of electrons is directed, the nozzle being configured to direct the spray of fluid substantially parallel and proximate to the exit window; and pumping the fluid to the nozzle assembly with a pump.

22. The method of claim 21 further comprising filtering particles from the fluid with a filter.

23. A method of sterilizing fluid comprising:

directing a spray of pressurized fluid from a nozzle assembly into a cavity of a sterilization chamber, the spray of fluid being a thin, flat film of fluid about 0.004 to 0.005 inches thick and irradiating the spray of fluid with a beam of electrons from an electron beam generator mounted to the sterilization chamber, the electron beam generator having an exit window through which the beam of electrons is directed, the nozzle being configured to direct the spray of fluid substantially parallel and proximate to the exit window.

24. A method of sterilizing fluid comprising:

directing a spray of pressurized fluid from a nozzle assembly into a cavity of a sterilization chamber, the spray of fluid being a thin, flat film of fluid;

irradiating the spray of fluid with a being of electrons from an electron beam generator mounted to the sterilization chamber, the electron beam generator having an exit window through which the beam of electrons is directed, the nozzle being configured to direct the spray of fluid substantially parallel and proximate to the exit window;

removing fluid that is sterilized front the cavity of the sterilization chamber through an outlet; and recycling a portion of the spray of fluid back for further irradiation through a recycling passage.

25. The method of claim 24 further comprising recycling an initial spray of fluid.

26. The method of claim 24 further comprising directing any fluid into the recycling passage that is unable to pass over a wall within the cavity between the cavity outlet and the recycling passage.

* * * * *

UNITED STATES PATENT AND TRADEMARK OFFICE
CERTIFICATE OF CORRECTION

PATENT NO. : 6,756,597 B2
DATED : June 29, 2004
INVENTOR(S) : Tzvi Avnery and Kenneth P. Felis It is certified that error appears in the above-identified patent and that said Letters Patent is hereby corrected as shown below:

Column 7,
Lines 37 and 55, delete "front" and insert -- from --.

Column 8,
Line 21, delete "abeam" and insert -- a beam --.

Column 9,
Line 12, delete "flu" and insert -- flat --.
Line 14, delete "mourning" and insert -- mounting --.
Line 35, delete "fanning" and insert -- forming --.
Line 43, delete "say" and insert -- any --.

Column 10,
Line 16, insert -- ; -- after "thick".
Line 29, delete "being" and insert -- beam --.
Line 36, delete "front" and insert -- from --.

Signed and Sealed this

Fifteenth Day of March, 2005

JON W. DUDAS
*Director of the United States Patent and Trademark Office*